United States Patent
Degenhardt et al.

(10) Patent No.: US 9,226,498 B2
(45) Date of Patent: Jan. 5, 2016

(54) SAFENING OF 4-AMINO-3-CHLORO-6-(4-CHLORO-2-FLUORO-3-METHOXYPHENYL)PYRIDINE-2-CARBOXYLIC ACID AND DERVIATIVES THEREOF ON CEREAL CROPS

(71) Applicants: Rory Degenhardt, Edmonton (CA); Bill McGregor, Beaumont (CA); Norbert M. Satchivi, Carmel, IN (US); Monte R. Weimer, Pittsboro, IN (US)

(72) Inventors: Rory Degenhardt, Edmonton (CA); Bill McGregor, Beaumont (CA); Norbert M. Satchivi, Carmel, IN (US); Monte R. Weimer, Pittsboro, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/151,237

(22) Filed: Jan. 9, 2014

(65) Prior Publication Data

US 2014/0194286 A1 Jul. 10, 2014

Related U.S. Application Data

(60) Provisional application No. 61/751,017, filed on Jan. 10, 2013.

(51) Int. Cl.
*A01N 43/60* (2006.01)
*A01N 25/32* (2006.01)
*A01N 43/40* (2006.01)

(52) U.S. Cl.
CPC ............... *A01N 25/32* (2013.01); *A01N 43/40* (2013.01)

(58) Field of Classification Search
None
See application file for complete search history.

(56) References Cited

U.S. PATENT DOCUMENTS

| | | |
|---|---|---|
| 7,314,849 B2 | 1/2008 | Balko et al. |
| 8,536,331 B2 | 9/2013 | Eckelbarger et al. |
| 2009/0215625 A1 | 8/2009 | McElroy et al. |
| 2010/0130362 A1 | 5/2010 | Satchivi et al. |
| 2011/0287932 A1* | 11/2011 | Hacker et al. ............... 504/103 |

FOREIGN PATENT DOCUMENTS

WO PCT/US2014/010847 4/2014

* cited by examiner

*Primary Examiner* — Alton Pryor
(74) *Attorney, Agent, or Firm* — Michael J. Terapane; Michael R. Asam

(57) ABSTRACT

Herbicidal injury that might otherwise be caused by 4-amino-3-chloro-6-(4-chloro-2-fluoro-3-methoxyphenyl)pyridine-2-carboxylic acid and agriculturally acceptable salt, ester, and amide derivatives thereof in cereal crops is reduced by concomitant application of florasulam.

11 Claims, No Drawings

SAFENING OF 4-AMINO-3-CHLORO-6-(4-CHLORO-2-FLUORO-3-METHOXYPHENYL)PYRIDINE-2-CARBOXYLIC ACID AND DERVIATIVES THEREOF ON CEREAL CROPS

CROSS REFERENCE TO RELATED APPLICATIONS

This application claims the benefit of U.S. Provisional Patent Application Ser. No. 61/751,017 filed Jan. 10, 2013, the disclosure of which is expressly incorporated herein by reference.

BACKGROUND

When agrochemicals, such as plant protection agents and especially herbicides, are used, the cultivated plants may be damaged to a certain degree, depending on factors such as the dose of agrochemicals and their method of application, the species of cultivated plant, the nature of the soil and climatic conditions, for example, length of time of exposure to light, temperature and amounts of precipitation. Thus, it is known that cultivated plants which are to be protected from the adverse effect of undesirable plant growth may be damaged to a certain degree under certain circumstances when an effective dose of herbicide is used. Various substances which are capable of specifically preventing the adverse effect of a herbicide on the cultivated plants, i.e., of protecting the cultivated plants without at the same time noticeably influencing the herbicidal action on weeds to be combated, have been proposed to solve this problem. Safening means preventing the adverse effect of a herbicide on the cultivated plants, i.e., protecting the cultivated plants without, at the same time, noticeably influencing the herbicidal action on weeds to be combated.

SUMMARY

It has now been found that, surprisingly, the phytotoxic effect of 4-amino-3-chloro-6-(4-chloro-2-fluoro-3-methoxyphenyl)pyridine-2-carboxylic acid and agriculturally acceptable salt, ester, and amide derivatives thereof, which might otherwise be observed on cereal crops such as wheat, barley, and tame oats, can be ameliorated by the concomitant application of florasulam. It is surprising that one herbicide can be safened by the concomitant application of a second herbicide.

Certain embodiments provided herein concern a method of protecting cereal plants from the harmful effects of a first herbicide which is the compound of the formula (I)

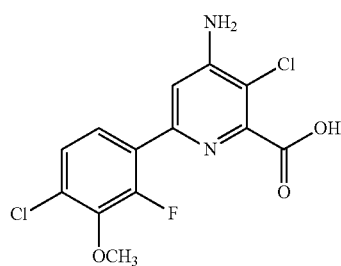

(I)

or an agriculturally acceptable salt, ester or amide derivative thereof, which comprises: concomitantly applying the first herbicide and florasulam to the cereal plant or to an area intended for cultivation of cereal plants.

The weight ratio of first herbicide to florasulam safener is between about 1:2 to about 35:1. In certain embodiments the first herbicide is the methyl ester of the compound of formula (I). In certain embodiments the first herbicide is the triethylamine (TEA) salt of the compound of formula (I). In certain embodiments the methyl ester or TEA salt of the compound of formula (I) is applied at a rate of about 2.5 to about 35 grams acid equivalent per hectare (g ae/ha), and the florasulam is applied at a rate of about 2.5 to 10 grams active ingredient per hectare (g ai/ha). In other embodiments the methyl ester or TEA salt of the compound of formula (I) is applied at a rate of about 5 to about 35 grams acid equivalent per hectare (g ae/ha), and the florasulam is applied at a rate of about 5 to 10 grams active ingredient per hectare (g ai/ha).

Provided herein are also compositions for protecting cereal plants from the harmful effects of a first herbicide which is a compound of the formula (I)

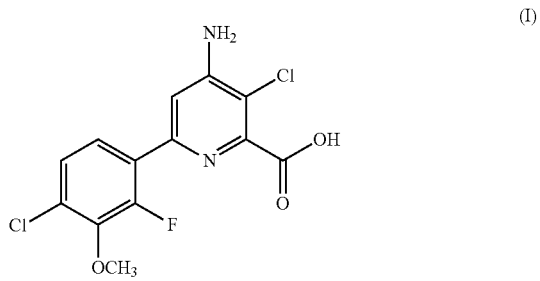 [SMILES: COc1c(Cl)ccc(-c2cc(N)c(Cl)c(C(=O)O)n2)c1F]

(I)

or an agriculturally acceptable salt, ester or amide derivative thereof, which comprises: said first herbicide and florasulam in a weight ratio of about 2:1 to about 1:2. In certain embodiments the first herbicide is the methyl ester or TEA salt of the compound of formula (I). In certain embodiments the weight ratio of first herbicide to florasulam is about 1:1.

It has been surprisingly found that the use of florasulam in combination with a first herbicide which is the compound of formula (I) or an agriculturally acceptable salt, ester, or amide derivative thereof exhibits a protecting effect against the phytotoxicity of the first herbicide on spring and winter wheat (*Triticum aestivum* L; TRZAS, TRZAW), durum wheat (*Triticum durum* L; TRZDU), spring and winter barley (*Hordeum vulgare* L; HORVS, HORVW) and tame oats (*Avena sativa*, AVESA) at herbicide-to-safener ratios between 1:2 and 35:1 without losing the herbicidal effects on weeds such as cleavers (*Galium aparine* L; GALAP), purple deadnettle (*Lamium purpureum* L; LAMPU), kochia (*Kochia scoparia* L; KCHSC), scented mayweed (*Matricaria chamomila* L; MATCH), corn poppy (*Papaver rhoeas* L; PAPRH), wild buckwheat (*Polygonum convolvulus* L; POLCO), Russian thistle (*Salsola iberica* L; SASKR), chickweed (*Stellaria media* L; STEME), bird's-eye speedwell (*Veronica persica* L; VERPE), wild pansy (*Viola tricolor* L; VIOTR).

DETAILED DESCRIPTION

4-Amino-3-chloro-6-(4-chloro-2-fluoro-3-methoxyphenyl)pyridine-2-carboxylic acid, i.e. the compound of formula (I), and its and agriculturally acceptable salts and esters thereof are described in U.S. Pat. No. 7,314,849 B2. Agriculturally acceptable amides are described in U.S. Pat. No. 8,536,331 B2. The compound of formula (I) and derivatives thereof control annual grass weeds and broadleaf weeds in wheat and barley but can be phytotoxic to cereals such as wheat and barley at commercially relevant herbicidal rates, which can be in the range of about 2.5 g ae/ha to about 35 g ae/ha or about 5 g ae/ha to about 35 g ae/ha. To be clear, at these rates the herbicides of formula (I) and derivatives thereof do not invariably or even consistently cause plant injury. However, because even occasional injury is undesirable, a method of protecting against injury is needed.

Florasulam is the common name for 2',6',8-trifluoro-5-methoxy[1,2,4]triazolo[1,5-c]pyrimidine-2-sulfonanilide. As described in Tomlin, C. D. S., Ed. *The Pesticide Manual: A World Compendium*, 15$^{th}$ ed.; BCPC: Alton, 2009 (hereafter "*The Pesticide Manual*, Fifteenth Edition, 2009"), page 508, florasulam is used for post-emergence control of broad-leaved weeds in cereals and maize at rates of up to 7.5 g ai/ha.

The term herbicide is used herein to mean an active ingredient that kills, controls or otherwise adversely modifies the growth of plants. A herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation. The term safener, as used herein, refers to a compound that selectively protects crop plants from herbicide damage without significantly reducing activity in target weed species.

Herbicidal activity is exhibited by the compounds when they are applied directly to the plant or to the locus of the plant via foliar, soil, or water application at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. In certain embodiments, the compositions provided herein are applied postemergence to relatively immature undesirable vegetation to achieve the maximum control of weeds.

The rates at which the compound of formula (I) or derivative thereof and florasulam are applied will depend upon the particular type of weed to be controlled, the degree of control required, and the timing and method of application. In certain embodiments about 2.5 to about 35 g ae/ha of the compound of formula (I) or derivative thereof and about 2.5 to about 10 g ai/ha of florasulam are applied. In other embodiments about 5 to about 35 g ae/ha of the compound of formula (I) or derivative thereof and about 5 to about 10 g ai/ha of florasulam are applied.

As used herein "concomitant" application means that the compound of formula (I) or derivative thereof and the florasulam safener are applied either separately or together as part of a multipart herbicidal system.

The herbicide-safener mixture of the compositions and methods provided herein can be applied in conjunction with one or more other herbicides to control a wider variety of undesirable vegetation. When used in conjunction with other herbicides, the composition can be formulated with the other herbicide or herbicides, tank-mixed with the other herbicide or herbicides or applied sequentially with the other herbicide or herbicides. Some of the herbicides that can be employed in conjunction with the safened composition provided herein include: 2,4-D esters and amines, acetochlor, acifluorfen, aclonifen, AE0172747, alachlor, amidosulfuron, aminocyclopyrachlor, aminotriazole, ammonium thiocyanate, anilifos, atrazine, AVH 301, azimsulfuron, benfuresate, bensulfuron-methyl, bentazone, benthiocarb, benzobicyclon, bifenox, bispyribac-sodium, bromacil, bromoxynil, butachlor, butafenacil, butralin, cafenstrole, carbetamide, carfentrazone-ethyl, chlorflurenol, chlorimuron, chlorpropham, cinosulfuron, clethodim, clomazone, clopyralid, cloransulam-methyl, cyclosulfamuron, cycloxydim, cyhalofop-butyl, dicamba, dichlobenil, dichlorprop-P, diclosulam, diflufenican, diflufenzopyr, dimethenamid, dimethenamid-p, diquat, dithiopyr, diuron, EK2612, EPTC, esprocarb, ethoxysulfuron, ethbenzanid, F7967, fenoxaprop, fenoxaprop-ethyl, fenoxaprop-ethyl+isoxadifen-ethyl, fentrazamide, flazasulfuron, fluazifop, fluazifop-P-butyl, flucetosulfuron, flufenacet, flufenpyr-ethyl, flumetsulam, flumiclorac-pentyl, flumioxazin, fluometuron, flupyrsulfuron, fluroxypyr, fomesafen, foramsulfuron, fumiclorac, glufosinate, glufosinate-ammonium, glyphosate, halosulfuron, haloxyfop-methyl, haloxyfop-R, imazamethabenz, imazamox, imazapic, imazapyr, imazaquin, imazethapyr, imazosulfuron, indanofan, iodosulfuron, ioxynil, IR 5790, isoproturon, isoxaben, isoxaflutole, KUH-021, lactofen, linuron, MCPA, MCPA ester and amine, mecoprop-P, mefenacet, mesosulfuron, mesotrione, metamifop, metolachlor, metosulam, metribuzin, metsulfuron, molinate, MSMA, napropamide, napropamide-M, nicosulfuron, norflurazon, OK-9701, orthosulfamuron, oryzalin, oxadiargyl, oxadiazon, oxazichlomefone, oxyfluorfen, paraquat, pendimethalin, penoxsulam, pentoxazone, pethoxamid, picloram, picolinafen, piperophos, pretilachlor, profoxydim, propachlor, propanil, propyzamide, prosulfocarb, prosulfuron, pyraclonil, pyraflufen-ethyl, pyrasulfotole, pyrazogyl, pyrazosulfuron, pyribenzoxim, pyriftalid, pyriminobac-methyl, primisulfuron, pyroxsulam, quinclorac, quizalofop-ethyl-D, S-3252, saflufenacil, sethoxydim, simazine, SL-0401, SL-0402, s-metolachlor, sulcotrione, sulfentrazone, sulfosate, tebuthiuron, terbacil, TH-547, thiazopyr, thiobencarb, triclopyr, triclopyr esters and amine, trifluralin and tritosulfuron.

The safened compositions provided herein can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. In certain embodiments, the herbicide-safener mixtures provided herein are used in combination with herbicides that are selective for the crop being treated and which complement the spectrum of weeds controlled by these compounds at the application rate employed. In certain embodiments, the safened compositions provided herein and other complementary herbicides are applied at the same time, either as a combination formulation or as a tank mix.

In certain embodiments, the safened composition of the present disclosure is utilized in mixtures containing a herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures provided herein are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99; paraffinic oil, alkoxylated alcohol non-ionic surfactant; mineral oil, surfactant blend.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

In certain embodiments, one or more surface-active agents are incorporated into the compositions provided herein. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like.

The compositions may also contain other compatible components, for example, other herbicides, plant growth regulators, fungicides, insecticides, and the like and can be formulated with liquid fertilizers or solid, particulate fertilizer carriers such as ammonium nitrate, urea and the like.

The concentration of the active ingredients in the herbicide-safener mixtures provided herein is, in some embodiments, from 0.001 to 98 percent by weight. Concentrations from 0.01 to 90 percent by weight are often employed. In compositions designed to be employed as concentrates, the active ingredients are in some embodiments present in a concentration from 5 to 98 weight percent, or in certain embodiments, 10 to 90 weight percent. Such compositions are typically diluted with an inert carrier, such as water, before application. The diluted compositions usually applied to weeds or the locus of weeds generally contain 0.0001 to 1 weight percent active ingredient. In certain embodiments, the diluted compositions contain 0.001 to 0.05 weight percent.

The present compositions can be applied to weeds or their locus by the use of conventional ground or aerial dusters, sprayers, and granule applicators, or irrigation water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Evaluation of Postemergence Herbicidal Safening in Cereal Crops

Five small plot field trials were established across various ecozones to evaluate the crop safety of florasulam and 4-amino-3-chloro-6-(4-chloro-2-fluoro-3-methoxy-phenyl) pyridine-2-carboxylic acid TEA (triethylamine) salt or of florasulam and 4-amino-3-chloro-6-(4-chloro-2-fluoro-3-methoxyphenyl)pyridine-2-carboxylic acid methyl ester, when applied alone or in combination, on spring cereals including spring wheat, spring barley and tame oats.

In Trials I and II the TEA salt of the compound of formula (I) was applied alone at rates of 17.5-35 g ae/ha using a formulation containing 30 grams acid equivalent per liter (g ae/L) TEA salt with 2.5% volume per volume (v/v) Assist adjuvant. Florasulam was applied alone using a formulation containing 50 grams active ingredient per liter (g ai/L) florasulam with 2.5% v/v Assist at a rate of 5 g ai/ha. The combination of TEA salt plus florasulam was applied as a straight tank-mix of the two above described formulations with 2.5% v/v Assist adjuvant at rates of 17.5 g ae/ha TEA salt plus 5 g ai/ha florasulam and 35 g ae/ha TEA salt plus 5 g ai/ha florasulam.

In Trials III, IV, and V the methyl ester of the compound of formula (I) was applied alone at rates of 5-10 g ae/ha using a formulation containing 200 grams acid equivalent per kilogram (g ae/kg) of the methyl ester with 0.5% v/v Turbocharge adjuvant. Florasulam was applied alone as Frontline XL (4 g ai/L florasulam+280 g ae/L 2-(4-chloro-2-methylphenoxy) acetic acid 2-ethylhexyl ester (MCPA ester) at a rate of 5 g ai/ha florasulam+350 g ae/ha MCPA ester. Although this treatment contained MCPA ester, it is to be noted that extensive trial work with Frontline XL has demonstrated no significant safening effect of the florasulam/MCPA combination relative to application of florasulam alone. The combination of the methyl ester plus florasulam was applied using a formulation containing 200 g ae/kg methyl ester+200 grams active ingredient per kilogram (g ai/kg) florasulam), with 0.5% v/v Turbocharge adjuvant, at rates of 5 g ae/ha methyl ester+5 g ai/ha florasulam and 10 g ae/ha methyl ester+10 g ai/ha florasulam. All herbicide treatments were applied post-emergence in the spring to early summer Herbicides were applied with bicycle- or tractor-mounted sprayers using carbon dioxide ($CO_2$) as a propellant. The sprayers delivered a uniform spray pattern that provided thorough coverage of the foliage using a 100 liter per hectare (L/ha) spray volume. At the time of herbicide applications, spring barley, spring wheat and tame oats were at the two leaf stage to the seven leaf, three tiller stage. Phytotoxicity to cereal crops was visually assessed as percent overall injury, compared to an untreated control plot. The overall injury assessments were based on visual ratings of growth inhibition, chlorosis, and delay in maturity. At late ratings, percent visual seed head deformity was also assessed. Trials were designed as randomized complete blocks with four replicates. In general, three to four replicates were assessed for each treatment.

Colby's equation was used to determine the herbicidal effects expected from the mixtures (Colby, S. R. Calculation of the synergistic and antagonistic response of herbicide combinations. *Weeds* 1967, 15, 20-22). Colby's equation is:

Expected=$A+B-(A \times B/100)$

A=observed efficacy of active ingredient A at the same concentration as used in the mixture;
B=observed efficacy of active ingredient B at the same concentration as used in the mixture.

For purposes of applying Colby's equation to determine the expected injury from applying 10 g ai/ha of florasulam in combination with the methyl ester of the compound of formula (I) in Trials III, IV, and V, it was assumed that the injury from 10 g ai/ha of florasulam alone would be the same as the injury observed for 5 g ai/ha of florasulam alone. If anything, this understated the expected injury of the combination using the higher rate of florasulam.

Crop safening by florasulam was assessed based on a negative difference between Colby's expected additive response and the observed response. Based on results obtained, the combination of post-emergence applied florasulam at 5-10 g ai/ha significantly reduces injury to spring barley, spring wheat and tame oats caused by herbicides of formula (I) and derivatives thereof at 5-35 g ae/ha.

The following Tables 1-6 summarize the observations in Trials I-V. Abbreviations used in the tables include:
DAT=days after treatment
g ai/ha=grams active ingredient per hectare
g ae/ha=grams acid equivalent per hectare
Obs=observed efficacy of the mixture
Exp=expected efficacy of the mixture as determined by Colby's equation The values reported in Tables 1-6 are means. Means followed by the same letter do not significantly differ (P=0.05, Tukey's HSD).

TABLE 1

Trial I. Safening effect when florasulam is applied in combination with 4-amino-3-chloro-6-(4-chloro-2-fluoro-3-methoxy-phenyl)pyridine-2-carboxylic acid TEA salt (Compound I) on spring wheat (TRZAS)

| Treatment | | Percent (%) Visual Injury | | Percent (%) Visual Incidence Head Deformity | |
|---|---|---|---|---|---|
| Compound I | Florasulam | 71 DAT | | 71 DAT | |
| g ae/ha | g ai/ha | Obs | Exp | Obs | Exp |
| 17.5 | | 12.5 cd | | 20 d-g | |
| 35 | | 32.5 a | | 60 a | |
| | 5 | 0 e | | 0.0 g | |
| 17.5 | 5 | 2.5 de | 12.5 | 2.5 fg | 20 |
| 35 | 5 | 2.5 de | 32.5 | 5.0 efg | 60 |

Note:
In this trial, 0% injury or negligible injury was observed for both control and mixture treatments at 8, 19, and 33 DAT on TRZAS.

TABLE 2

Trial II. Safening effect when florasulam is applied in combination with 4-amino-3-chloro-6-(4-chloro-2-fluoro-3-methoxy-phenyl)pyridine-2-carboxylic acid TEA salt (Compound I) on spring wheat (TRZAS)

| Treatment | | Percent (%) Visual Injury | | Percent (%) Visual Incidence Head Deformity | |
|---|---|---|---|---|---|
| Compound I | Florasulam | 55 DAT | | 55 DAT | |
| g ae/ha | g ai/ha | Obs | Exp | Obs | Expected |
| 17.5 | | 5.8 de | | 7.5 cde | |
| 35 | | 35 a | | 43.8 ab | |
| | 5 | 0.0 e | | 0.0 e | |
| 17.5 | 5 | 1.3 e | 5.8 | 2.5 de | 7.5 |
| 35 | 5 | 8.8 cde | 35 | 8.8 cde | 43.8 |

Note:
In this trail, 0% injury was observed for both controls and mixture treatments at 6, 14 and 31 DAT on TRZAS.

TABLE 3

Trial III. Safening effect when florasulam is applied in combination with 4-amino-3-chloro-6-(4-chloro-2-fluoro-3-methoxy-phenyl)pyridine-2-carboxylic acid methyl ester (Compound II) on tame oats (AVESA)

| Treatment | | | Percent (%) Visual Injury 7 DAT | | Percent (%) Visual Injury 16 DAT | | Percent (%) Visual Injury 31 DAT | | Percent (%) Visual Injury 70 DAT | | Percent (%) Visual Head Deformity 70 DAT | |
|---|---|---|---|---|---|---|---|---|---|---|---|---|
| Compound II | Florasulam | MCPA Ester g | | | | | | | | | | |
| g ae/ha | g ai/ha | ae/ha | Obs | Exp | Obs | Exp | Obs | Exp | Obs | Exp | Obs | Exp |
| 5 | | | 0.0 d | | 2.5 de | | 5.0 fg | | 15.8 def | | 7.5 cd | |
| 10 | | | 0.0 d | | 13.8 cde | | 25.0 de | | 33.8 bcd | | 15.0 bcd | |
| | 5 | 350 | 17.5 bc | | 0.0 e | | 0.8 g | | 0.0 f | | 0.0 d | |

TABLE 3-continued

Trial III. Safening effect when florasulam is applied in combination with 4-amino-3-chloro-6-(4-chloro-2-fluoro-3-methoxy-phenyl)pyridine-2-carboxylic acid methyl ester (Compound II) on tame oats (AVESA)

| Treatment | | | Percent (%) Visual Injury 7 DAT | | Percent (%) Visual Injury 16 DAT | | Percent (%) Visual Injury 31 DAT | | Percent (%) Visual Injury 70 DAT | | Percent (%) Visual Head Deformity 70 DAT | |
|---|---|---|---|---|---|---|---|---|---|---|---|---|
| Compound II g ae/ha | Florasulam g ai/ha | MCPA Ester g ae/ha | Obs | Exp | Obs | Exp | Obs | Exp | Obs | Exp | Obs | Exp |
| 5 | 5 | | 18.8 bc | 17.5 | 1.3 e | 2.5 | 0.8 g | 5.8 | 6.3 f | 15.8 | 0.0 d | 7.5 |
| 10 | 10 | | 38.8 a | 17.5 | 4.5 de | 13.8 | 2.3 g | 25.6 | 7.5 f | 33.8 | 0.0 d | 15 |

Note:
In this trial, 0% injury was observed for both controls and mixture treatments at 7, 16, 31, and 74 DAT on HORVS (spring barley), at 7, 16, 31, and 79 DAT on TRZAS (spring wheat), and at 7, 16, 31, 79, and 113 DAT on TRZDU (Durum wheat).

TABLE 4

Trial IV. Safening effect when florasulam is applied in combination with 4-amino-3-chloro-6-(4-chloro-2-fluoro-3-methoxy-phenyl)-pyridine-2-carboxylic acid methyl ester (Compound II) on tame oats (AVESA)

| Treatment | | | Percent (%) Visual Injury 7 DAT | | Percent (%) Visual Injury 14 DAT | | Percent (%) Visual Injury 28 DAT | | Percent (%) Visual Injury 53 DAT | |
|---|---|---|---|---|---|---|---|---|---|---|
| Compound II g ae/ha | Florasulam g ai/ha | MCPA Ester g ae/ha | Observed | Expected | Observed | Expected | Observed | Expected | Observed | Expected |
| 5 | | | 0.0 d | | 2.0 cde | | 3.3 de | | 2.5 fgh | |
| 10 | | | 1.3 bcd | | 9.5 abc | | 14.5 ab | | 9.4 abc | |
| | 5 | 350 | 5.8 abc | | 0.8 de | | 0.0 e | | 0.6 gh | |
| 5 | 5 | | 4.0 a-d | 5.8 | 1.5 cde | 2.8 | 0.8 a | 3.3 | 0.3 h | 3.1 |
| 10 | 10 | | 7.5 a | 7.0 | 2.5 b-e | 10.2 | 2.8 de | 14.5 | 1.0 gh | 9.9 |

Note:
In this trial, 0% injury was observed for both controls and mixture treatments at 7, 14, 28, and 53 DAT on TRZAS and TRZDU.

TABLE 5

Trial IV cont. Safening effect when florasulam is applied in combination with 4-amino-3-chloro-6-(4-chloro-2-fluoro-3-methoxy-phenyl)-pyridine-2-carboxylic acid methyl ester (Compound II) on spring barley (HORVS)

| Treatment | | | Percent (%) Visual Injury 7 DAT | | Percent (%) Visual Injury 14 DAT | | Percent (%) Visual Injury 28 DAT | | Percent (%) Visual Injury 70 DAT | | Percent (%) Visual Head Deformity | |
|---|---|---|---|---|---|---|---|---|---|---|---|---|
| Compound II g ae/ha | Florasulam g ai/ha | MCPA Ester g ae/ha | Obs | Exp | Obs | Exp | Obs | Exp | Obs | Exp | Obs | Exp |
| 5 | | | 0.0 e | | 0.0 c | | 3.3 de | | 2.5 fgh | | 0.0 a | |
| 10 | | | 0.0 e | | 0.0 c | | 14.5 ab | | 9.4 abc | | 1.3 a | |
| | 5 | 350 | 2.3 cde | | 0.8 bc | | 0.0 e | | 0.6 gh | | 0.0 a | |
| 5 | 5 | | 2.8 cde | 2.3 | 2.5 abc | 0.8 | 0.8 e | 3.3 | 0.3 h | 3.1 | 0.0 a | 0.0 |
| 10 | 10 | | 4.0 a-d | 2.3 | 0.0 c | 0.8 | 2.8 de | 14.5 | 1.0 gh | 9.9 | 0.0 a | 1.3 |

TABLE 6

Trial V. Safening effect when florasulam is applied in combination with 4-amino-3-chloro-6-(4-chloro-2-fluoro-3-methoxy-phenyl)-pyridine-2-carboxylic acid methyl ester (Compound II) on spring barley (HORVS)

| Treatment | | | Percent (%) Injury Visual 15 DAT | | Percent (%) Visual Injury 27 DAT | | Percent (%) Visual Injury 49 DAT | | Percent (%) Head Deformity 64 DAT | |
|---|---|---|---|---|---|---|---|---|---|---|
| Compound II g ae/ha | Florasulam g ai/ha | MCPA Ester g ae/ha | Obs | Exp | Obs | Exp | Obs | Exp | Obs | Exp |
| 5 | | | 0.5 a | | 1.0 c | | 0.0 c | | 0.3 b | |
| 10 | | | 0.5 a | | 0.0 c | | 0.5 bc | | 21.8 ab | |
| | 5 | 350 | 2.0 a | | 7.8 a | | 1.0 bc | | 0.3 b | |

TABLE 6-continued

Trial V. Safening effect when florasulam is applied in combination with 4-amino-3-chloro-6-(4-chloro-2-fluoro-3-methoxy-phenyl)-pyridine-2-carboxylic acid methyl ester (Compound II) on spring barley (HORVS)

| Treatment | | | Percent (%) Injury Visual 15 DAT | | Percent (%) Visual Injury 27 DAT | | Percent (%) Visual Injury 49 DAT | | Percent (%) Head Deformity 64 DAT | |
|---|---|---|---|---|---|---|---|---|---|---|
| Compound II | Florasulam | MCPA Ester | | | | | | | | |
| g ae/ha | g ai/ha | g ae/ha | Obs | Exp | Obs | Exp | Obs | Exp | Obs | Exp |
| 5 | 5 | 4.0 a | 2.5 | 3.5 abc | 8.7 | 0.0 c | 1.0 | 0.3 b | 0.6 | |
| 10 | 10 | 2.0 a | 2.5 | 7.3 ab | 7.8 | 0.0 c | 1.5 | 0.8 b | 22.0 | |

What is claimed is:

1. A method of protecting cereal plants from the harmful effects of a first herbicide which is the compound of the formula (I)

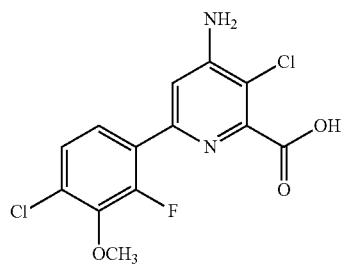

(I)

or an agriculturally acceptable salt, ester or amide derivative thereof, which comprises: concomitantly applying the first herbicide and florasulam to the cereal plant or to an area intended for cultivation of cereal plants, wherein the amount of injury to the cereal plants is reduced compared to when compound (I) is applied without the concomitant application of florasulam.

2. The method of claim 1, wherein the first herbicide is applied at a rate of from about 2.5 to about 35 g ae/ha, and the florasulam is applied at a rate of from about 2.5 to about 10 g ai/ha.

3. The method of claim 1, wherein the first herbicide is applied at a rate of from about 5 to about 35 g ae/ha, and the florasulam is applied at a rate of from about 5 to about 10 g ai/ha.

4. The method of claim 1, wherein the first herbicide is the methyl ester or the triethylamine (tea) salt of the compound of formula (i).

5. The method of claim 4, wherein the methyl ester or tea salt is applied at a rate of from about 2.5 to about 10 g ae/ha.

6. The method of claim 4, wherein the methyl ester or tea salt is applied at a rate of from about 5 to about 10 g ae/ha.

7. The method of claim 1, wherein the cereal plant is wheat, barley, or tame oats.

8. The method of claim 1, wherein the first herbicide and florasulam are applied together.

9. A composition effective in protecting cereal plants from the harmful effects of a first herbicide which is the compound of formula (I)

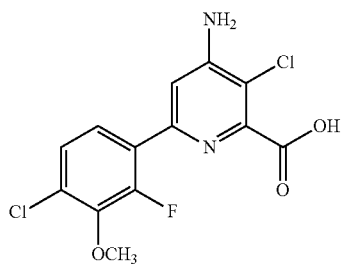

(I)

or an agriculturally acceptable salt, ester or amide derivative thereof, which comprises: said first herbicide in combination with an effective safening amount of florasulam, wherein the first herbicide to the forasulam is in a weight ratio of about 2:1 to about 1:2.

10. The composition of claim 9, wherein the weight ratio of said first herbicide to florasulam is about 1:1.

11. The composition of claim 9, wherein the herbicide is the methyl ester or tea salt of the compound of formula (i).

* * * * *